(12) United States Patent
Friedrich

(10) Patent No.: US 10,689,522 B2
(45) Date of Patent: *Jun. 23, 2020

(54) FLUORINE COMPOUNDS

(71) Applicant: Merck Patent GmbH, Darmstadt (DE)

(72) Inventor: Reiner Friedrich, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/536,700

(22) PCT Filed: Dec. 16, 2015

(86) PCT No.: PCT/EP2015/002528
§ 371 (c)(1),
(2) Date: Jun. 16, 2017

(87) PCT Pub. No.: WO2016/096128
PCT Pub. Date: Jun. 23, 2016

(65) Prior Publication Data
US 2017/0349761 A1 Dec. 7, 2017

(30) Foreign Application Priority Data

Dec. 19, 2014 (EP) .................... 14004336

(51) Int. Cl.
| | | |
|---|---|---|
| *C09D 5/00* | (2006.01) | |
| *C07F 7/18* | (2006.01) | |
| *C07C 69/653* | (2006.01) | |
| *C09D 4/00* | (2006.01) | |
| *C09D 183/08* | (2006.01) | |

(52) U.S. Cl.
CPC .............. *C09D 5/00* (2013.01); *C07C 69/653* (2013.01); *C07F 7/1804* (2013.01); *C09D 4/00* (2013.01); *C09D 183/08* (2013.01)

(58) Field of Classification Search
None
See application file for complete search history.

(56) References Cited

U.S. PATENT DOCUMENTS

| | | | |
|---|---|---|---|
| 5,679,738 A | 10/1997 | Bafford et al. | |
| 6,809,216 B2 | 10/2004 | Bradley | |
| 7,294,731 B1 | 11/2007 | Flynn et al. | |
| 7,745,653 B2 | 6/2010 | Iyer et al. | |
| 8,507,601 B2 | 8/2013 | Brown | |
| 8,669,336 B2 | 3/2014 | Moeck | |
| 2011/0084227 A1* | 4/2011 | Brown | D06M 15/564 252/8.62 |

FOREIGN PATENT DOCUMENTS

| | | |
|---|---|---|
| CN | 101501046 A | 8/2009 |
| CN | 101679461 A | 3/2010 |
| GB | 1511992 A | 5/1978 |
| JP | 9132615 A | 5/1997 |
| JP | 2004300332 A | 10/2001 |
| JP | 2003268042 A | 9/2003 |
| WO | 2002103103 A1 | 12/2002 |
| WO | 2009103613 A1 | 8/2009 |
| WO | 2011056525 A1 | 5/2011 |
| WO | 2015133532 A1 | 9/2015 |
| WO | 2016096128 A1 | 6/2016 |

OTHER PUBLICATIONS

A. A. Ll'In et al., Russian Journal of Applied Chemistry, vol. 80, No. 3, 2007, pp. 405-418.
Paleta O et al: "Radical addition reactions of fluorinated species Part 6. Regioselectivity of the addition of nucleophilic radicals to halogenopropenes and evidence for a steric effect of the chlorine substituent", Journal of Fluorine Chemistry, Elsevier, NL, vol. 86, No. 2, Dec. 5, 1997 (Dec. 5, 1997), pp. 155-171, XP004107216, ISSN: 0022-1139, DOI: 10.1016/S0022-1139(97)00083-3.
T M Aleksandrova et al: "Modification of the Surface Properties of Cellulose Materials by Grafting Fluoralkyl(Meth)Acrylates", Polymer Science U.S.S.R., vol. 13, No. 11, Jan. 1, 1971 (Jan. 1, 1971), pp. 2595-2600, XP055249073.
International Search report PCT/EP2015/002528 dated May 10, 2016.
Office Action dated Aug. 24, 2018 in corresponding Europen application No. 15817071.2 (pp. 1-6).
Gorbunova et al., Seriya Khimicheskaya, 1992, vol. 2, pp. 408-412.
Office Action in corresponding CN 201580069291.2 dated Dec. 5, 2019 (pp. 1-10).
Office Action in corresponding JP 2017-532681 dated Sep. 9, 2019 (pp. 1-8).

* cited by examiner

*Primary Examiner* — Clinton A Brooks
(74) *Attorney, Agent, or Firm* — Millen White Zelano & Branigan

(57) ABSTRACT

The present invention relates to compounds of the formula (I) $(Rf-CHF-CF_2-CHR)_m-L-(X)_n$, where Rf=a perfluorinated alkyl group, optionally containing heteroatoms, R=H or an alkyl group, L=a single bond or a divalent organic group, X=an anchor group, m is $\geq 1$ and n is $\geq 1$, and to the use thereof in, for example, dirt-repellent coatings.

18 Claims, No Drawings

FLUORINE COMPOUNDS

The present invention relates to novel compounds containing fluorinated end groups and to the use thereof in, for example, dirt-repellent coatings Dirt-repellent coatings in the textile industry consist principally of perfluorinated compounds which can be bonded to surfaces by means of acrylate, methacrylate or siloxane groups. Dirt-repellent coatings, for example in the display industry, consist principally of perfluorinated compounds which can be bonded to surfaces by means of siloxane groups. Owing to their chemical stability, these compounds have been criticised over the years since the perfluorinated content of this class of materials cannot be degraded by natural means. In addition, it has not unambiguously been clarified what influence these long-lived materials have on the biosphere and whether they result in bioaccumulation in various animal species.

There is therefore a need for alternative substances for dirt-repellent coatings.

The present invention relates firstly to compounds of the formula (I)

$$(Rf\text{-}CHF\text{-}CF_2\text{-}CHR)_m\text{-}L\text{-}(X)_n \quad (I)$$

where
Rf=a perfluorinated alkyl group, optionally containing heteroatoms,
R=H or an alkyl group,
L=a single bond or a divalent organic group,
X=an anchor group,
M is ≥1
and n is ≥1.

The perfluorinated group Rf is preferably selected from the groups:
$CF_3-(CF_2)_{0-3}-$, $CF_3-(CF_2)_{0-3}-O-$, $CF_3-(CF_2)_{0-3}-O-(CF_2)_{1-3}-$, $CF_3-(CF_2)_{0-3}-(CF_2)_{1-3}-O-$, $CF_3-(CF_2)_{0-3}-O-(CF_2)_{1-3}-O-CF_2-$, $CF_3-(CF_2)_{0-3}O-(CF_2-O)_{1-8}-$ and $CF_3-(CF_2)_{0-3}-O-(CF_2-O)_{1-8}-CF_2-$.

The perfluorinated group Rf is particularly preferably selected from the groups:
$CF_3-(CF_2)_{1-2}-$, $CF_3-(CF_2)_{1-2}-O-$, $CF_3-O-(CF_2)_{1-2}-$, $CF_3-O-(CF_2)_{1-3}-O-$, $CF_3-(CF_2)_{1-2}-O-CF_2-$, $CF_3-O-(CF_2)_{1-2}-O-CF_2-$, $CF_3-O-(CF_2-O)_{1-8}-$ and $CF_3-O-(CF_2-O)_{1-8}-CF_2-$.

In a variant, the perfluorinated group Rf can also preferably be selected from the groups $CF_3-(CF_2)_{0-3}-$, $CF_3-(CF_2)_{0-3}-O-$, $CF_{3-0}-(CF_2)_{1-3}-$ and $CF_3-O-(CF_2)_{1-3}-O-$, in particular from the groups $CF_3-(CF_2)_{1-2}-$, $CF_3-(CF_2)_{1-2}-O-$, $CF_3-O-(CF_2)_{1-2}-$ and $CF_3-O-(CF_2)_{1-2}-O-$.

The group R is preferably equal to H or C1-C3 alkyl, in particular H or a methyl group.

L is preferably a single bond or a saturated or unsaturated, branched or unbranched hydrocarbon unit, optionally containing heteroatoms and/or functional groups. L is particularly preferably a single bond or a saturated, branched or unbranched alkylene group, optionally containing heteroatoms and/or functional groups.

The group X is an anchor group which is suitable for facilitating adhesion of the compounds of the formula (I) to substrate surfaces, such as, for example, textiles or glass surfaces. In other words, the group X is preferably a reactive group which forms a covalent bond to substrate surfaces. X is preferably an ethylenically unsaturated group, in particular an acrylate or methacrylate group, an alkoxysilane group or a halosilane group. X can be an $-SiR'_3$ group, where the R' groups are, independently of one another, equal to alkyl, OH, halogen, alkoxy or aryloxy, where at least one group R' is not an alkyl group. R' is preferably an alkoxy group OR", where R" is equal to C1-C4-alkyl, in particular C1- or C2-alkyl. In particular for bonding to glass surfaces, X is preferably an alkoxysilane group $-Si(OR"_3)_3$, where R" is equal to C1-C4-alkyl, in particular C1- or C2-alkyl.

In a particularly preferred variant of the invention, in particular for bonding to textile surfaces, X is preferably an acrylate or methacrylate group.

m is preferably 1-3, in particular 1 or 2.
n is preferably 1-3, in particular 1.

Particularly advantageous are compounds of the formula (I) in which one or more of the variables have the preferred meanings. Compounds in which all variables have the preferred meanings are especially advantageous. Particular preference is given to compounds where:
Rf=$CF_3-(CF_2)_{1-2}-$, $CF_3-(CF_2)_{1-2}-O-$, $CF_3-O-(CF_2)_{1-2}-$, $CF_3-O-(CF_2)_{1-3}-O-$, $CF_3-(CF_2)_{1-2}-O-CF_2-$, $CF_3-O-(CF_2)_{1-2}-O-CF_2-$, $CF_3-O-(CF_2-O)_{1-8}-$ and $CF_3-O-(CF_2-O)_{1-8}-CF_2-$,
R=H or $CH_3$,
L=a single bond or a C1-C4-alkylene group, which is optionally branched and/or contains heteroatoms, in particular O, and/or a functional group, in particular OH,
X=an acrylate or methacrylate group, and
m=1 or 2 and n=1.

Particular preference is also given to compounds where:
Rf=$CF_3-(CF_2)_{1-2}-$, $CF_3-(CF_2)_{1-2}-O-$, $CF_3-O-(CF_2)_{1-2}-$, $CF_3-O-(CF_2)_{1-3}-O-$, $CF_3-(CF_2)_{1-2}-O-CF_2-$, $CF_3-O-(CF_2)_{1-2}-O-CF_2-$, $CF_3-O-(CF_2-O)_{1-8}-$ and $CF_3-O-(CF_2-O)_{1-8}-CF_2-$,
R=H or $CH_3$,
L=a single bond or a C1-C4-alkylene group, which is optionally branched and/or contains heteroatoms, in particular O, and/or a functional group, in particular OH,
X=an alkoxysilane group $-Si(OR"_3)_3$, where R" is equal to C1- or C2-alkyl, and m=1 or 2 and n=1.

An advantage of the novel compounds is that they are readily degradable. They have specific nominal breaking points in the molecule. Thus, corresponding low-molecular-weight fragments are able to form, which are able to enter the atmosphere and can thus be decomposed in the stratosphere under UV light.

Hydrofluoroethers of the following structure can be converted into readily volatile and UV-decomposable compounds, for example by hydrolysis and oxidation. The decomposition products can then be washed out of the atmosphere with the rain, transferred into the ground and mineralised there.

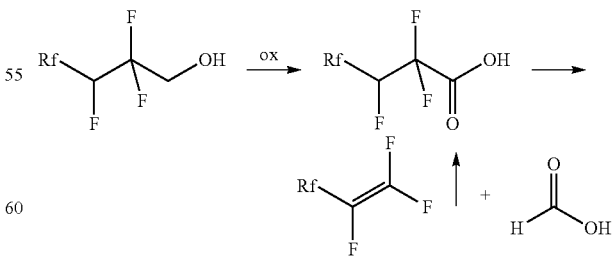

In addition, it may be advantageous if the hydrofluorether carries a further alkyl group in the a position to the hydroxyl group. This enables on the one hand an improvement to be achieved in the hydrolysis resistance, on the other hand it prevents oxidation of the alcohol group to the carboxylic acid. The oxidation product formed is consequently only the ketone, which in turn has a higher vapour pressure and is thus more volatile.

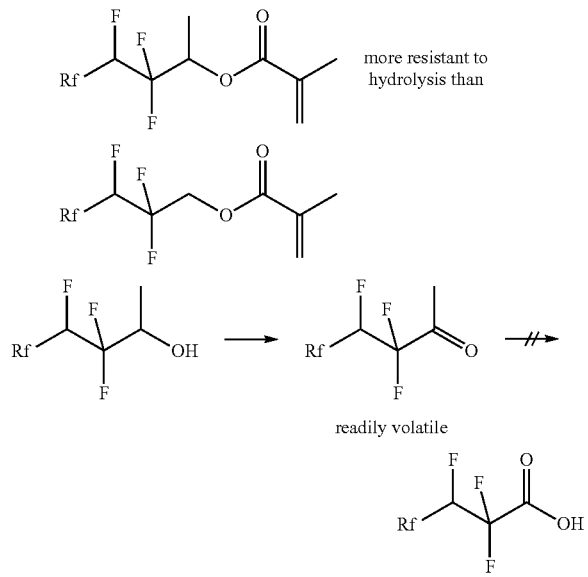

Particular preference is given to compounds of the formulae (II) to (VIII) in which Rf=a perfluorinated alkyl group, optionally containing heteroatoms, R''=C1-C4-alkyl, in particular C1- or C2-alkyl and R'''=H or an alkyl group, preferably is equal to H or methyl.

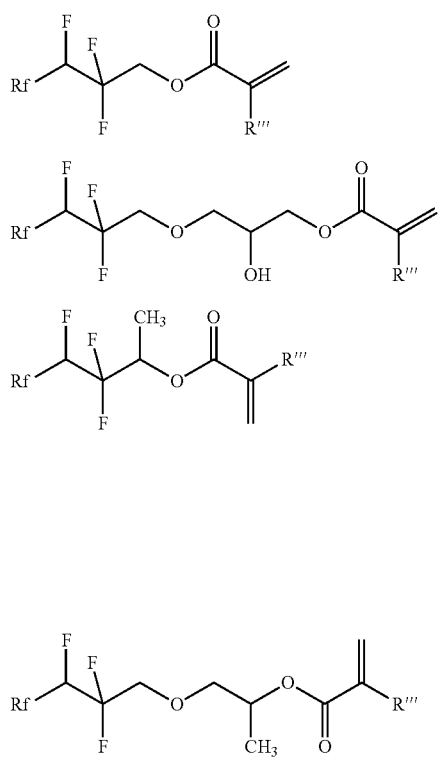

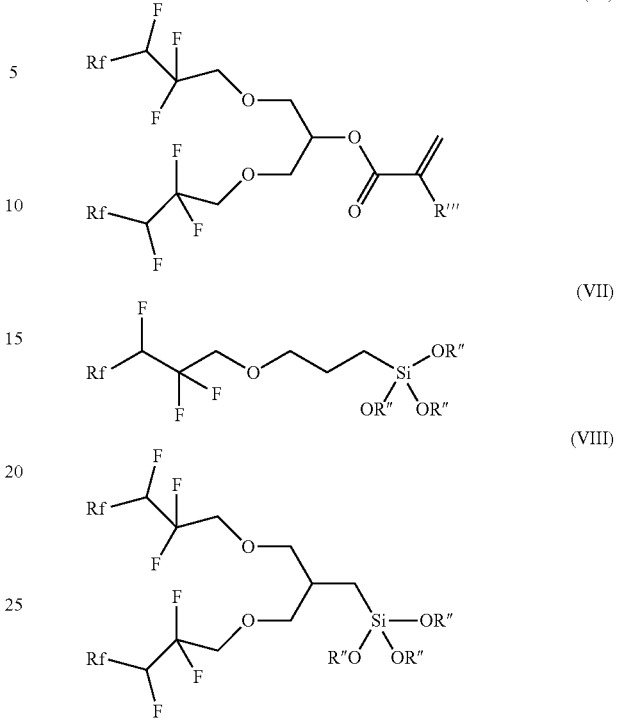

Preference is given to compounds of the formulae (II) to (VIII) in which the perfluorinated group Rf is selected from the groups:
$CF_3-(CF_2)_{0-3}-$, $CF_3-(CF_2)_{0-3}-O-$, $CF_3-(CF_2)_{0-3}-O-(CF_2)_{1-3}-$, $CF_3-(CF_2)_{0-3}-O-(CF_2)_{1-3}-O-$, $CF_3-(CF_2)_{0-3}-O-(CF_2)_{1-3}-O-CF_2-$, $CF_3-(CF_2)_{0-3}-O-(CF_2-O)_{1-8}-$ and $CF_3-(CF_2)_{0-3}-O-(CF_2-O)_{1-8}-CF_2-$.

Particular preference is given to compounds of the formulae (II) to (VIII) in which the perfluorinated group Rf is selected from the groups:
$CF_3-(CF_2)_{1-2}-$, $CF_3-(CF_2)_{1-2}-O-$, $CF_3-O-(CF_2)_{1-2}-$, $CF_3-O-(CF_2)_{1-3}-O-$, $CF_3-(CF_2)_{1-2}-O-CF_2-$, $CF_3-O-(CF_2)_{1-2}-O-CF_2-$, $CF_3-O-(CF_2-O)_{1-8}-$ and $CF_3-O-(CF_2-O)_{1-8}-CF_2-$.

In a variant, the perfluorinated group Rf may also preferably be selected from the groups $CF_3-(CF_2)_{0-3}-$, $CF_3-(CF_2)_{0-3}-O-$, $CF_3-O-(CF_2)_{1-3}-$ and $CF_{3-0}-(CF_2)_{1-3}-O-$, in particular from the groups $CF_3-(CF_2)_{1-2}-$, $CF_3-(CF_2)_{1-2}-O-$, $CF_3-O-(CF_2)_{1-2}-$ and $CF_3-O-(CF_2)_{1-2}-O-$.

In particular, preference is given to compounds of the formulae (II) to (VIII) in which Rf is one of the preferred or particularly preferred groups and R''=C1- or C2-alkyl and/or R'''=H or methyl.

The compounds of the formula (I) can easily be synthesised. The starting materials used for the preparation of the compounds of the formula (I) are commercially available and/or their preparation starting from commercially available starting materials is familiar to the person skilled in the art or they can be prepared analogously to known synthetic processes, for example free-radical addition see: A. A. Il'in et al., Russian Journal of Applied Chemistry, 2007, Vol. 80, No. 3, pp. 405-418.

The preferred compounds of the formula (I) can be achieved, for example, by the following simple synthesis, as is shown by way of example for the acrylates or methacrylates of the formulae (II) and (III):

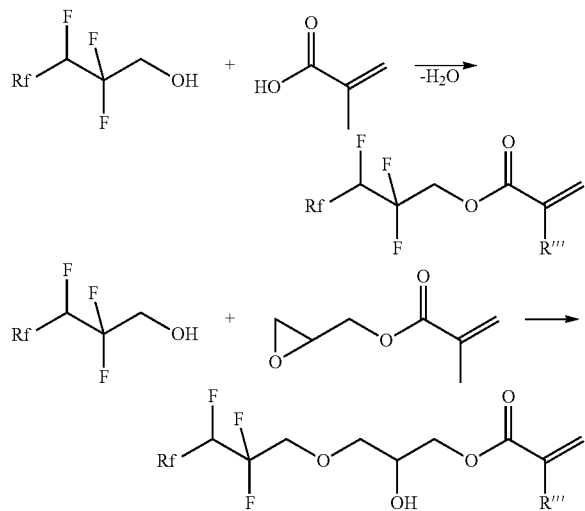

Compounds of the formula (I) which belong to the substance class of the organosilanes can be prepared, for example, by reaction of corresponding fluorine-containing olefins with silanes by methods known to the person skilled in the art.

The syntheses shown in the examples can be used analogously for further compounds of the formulae (I) to (VIII).

The degradation of the compounds of the formulae (I) to (VIII) can preferably be carried out by a process for the degradation of fluorine-containing compounds comprising the following steps:

a) biological and/or abiotic degradation of the carbon skeleton of the fluorine-containing compounds with formation of, preferably non-toxic, fluorine-containing compounds, preferably having an adequately high vapour pressure, b) conversion of the fluorine-containing compounds formed in step a) into a gas phase, c) degradation of the fluorine-containing compounds formed in step a) into low-molecular-weight compounds by UV irradiation in the gas phase, d) conversion of the low-molecular-weight compounds formed in step c) from the gas phase into a liquid and/or solid phase, e) mineralisation of the low-molecular-weight compounds formed step c) in the liquid and/or solid phase.

Preferably, no fluorine-containing, salts are formed in step a). In particular, no perfluorinated compounds are formed in step a). The fluorine-containing compounds formed in step a) preferably have a sufficiently high vapour pressure in order to enable them to convert or be converted easily into the gas phase, preferably at atmospheric pressure.

The compounds according to the invention can be used alone or in the form of a mixture, also with other fluorinated and/or non-fluorinated compounds, in particular for the production of functional coatings and surface modifications of all types on articles both for inside and outside areas. In principle, all surfaces can be coated, in particular glass, ceramic, enamel, metals, plastics, elastomers, natural products, textiles, if necessary after suitable pretreatment.

The present invention furthermore relates to the use of the compounds of the formula (I) to (VIII) according to the invention and the preferred embodiments described above for the production of, for example, dirt-repellent and/or hydrophobic, coatings, in particular also for textile finishing and glass coating.

Besides the compounds of the formula (I), the coatings may also comprise solvents, additives, surfactants, assistants and fillers. Mention may also be made by way of example of silicone particles and, optionally surface-modified, pigments.

Preferred areas of use are, for example, the use of the compounds according to the invention in coatings for optical elements or textiles, such as, for example, the use in anti-fingerprint coatings, for example for displays, optical lenses, spectacle lenses, camera lenses, binoculars, window panes or mirrors, or as hydrophobicising agents for textile finishing.

The compounds according to the invention or mixtures comprising them can be applied to a suitable surface, over the entire area or a part-area, by various coating processes known to the person skilled in the art, for example by means of CVD, PVD, spray coating, ink-jet, offset processes.

The present invention relates to all uses mentioned here of compounds to be employed in accordance with the invention. The respective use of compounds of the formula (I) for the said purposes is known to the person skilled in the art, and consequently the use of the compounds to be employed in accordance with the invention causes no problems.

The invention also relates to compositions which comprise at least one of the compounds according to the invention, where the compositions may also comprise solvents, additives, surfactants, assistants and fillers.

The invention also relates to coated articles, in particular the above-mentioned articles, whose coating has been produced using at least one compound according to the invention. Preference is given to displays, optical lenses, spectacle lenses, camera lenses, binoculars, window panes, mirrors and textiles.

The following examples explain the present invention in greater detail without restricting the scope of protection.

EXAMPLES

Abbreviations

TEMPO 2,2,6,6-tetramethylpiperidinyloxyl
THF tetrahydrofuran
MTBE tert-butyl methyl ether
RT room temperature Example 1: Synthesis of the Compound of Formula (IVa)

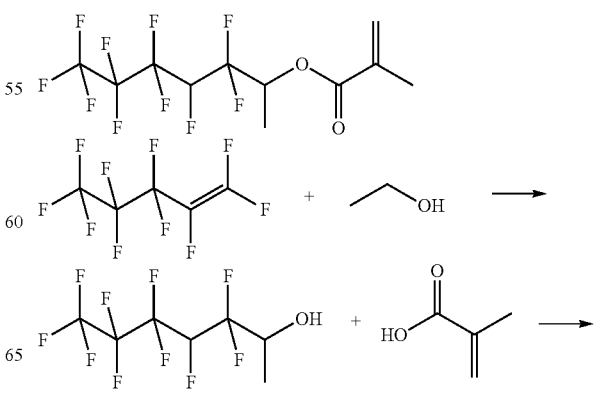

-continued

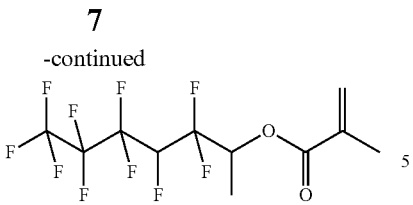

5 g of decafluoropentene are stirred with 8 g of ethanol and 0.2 g of benzoyl peroxide at 100° C. in an autoclave for 18 h. The crude product is distilled. Yield: 2.5 g b.p. 50° C. at 3.5 mbar.

The hydrofluoroalcohol is warmed under reflux at 110° C. with methacrylic acid and toluene on a water separator for 24 h. The catalyst employed is p-toluenesulfonic acid and TEMPO.

The product is subsequently distilled.

Example 2: Synthesis of the Compound of the Formula (IIIa)

(IIIa)

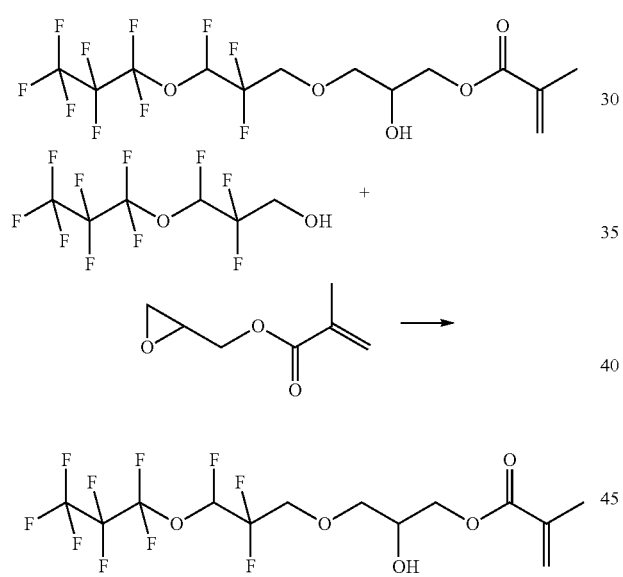

4.0 g of 2,3-epoxypropyl methacrylate and 10.9 g of 2,2,3-trifluoro-3-heptafluoropropyloxypropan-1-ol are initially introduced in a two-necked flask. 3.2 g of potassium tert-butoxide in 20.3 g of THF are added dropwise with cooling. The reaction mixture is subsequently heated to 100° C. and stirred at this temperature for 24 h.

20 ml of water and 20 ml of MTBE are added to the reaction mixture, and the phases are separated. The aqueous phase is extracted with 2×30 ml of MTBE, and the combined organic phase is washed with 40 ml of water and 40 ml of saturated NaCl solution. The extract is dried over sodium sulfate, and the solvent is distilled.

Product weight: 14.02 g

1H-NMR: 6.8 ppm (dt, 2H, —CFH); 6.4 ppm (d, 2H, =CH2); 4.2-4.4 ppm (m, 3H, —CH2-CHO); 3.4-3.6 ppm (m, 4H, CF2-CH2-O—CH2); 2.0 ppm (s, 3H, —CH3);

Example 3: Synthesis of the Compound of the Formula (Va)

(Va)

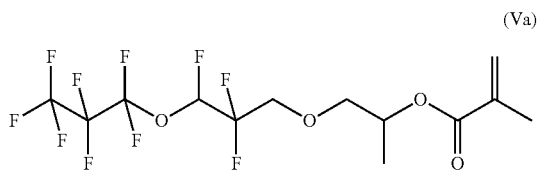 [SMILES: C=C(C)C(=O)OC(C)COCC(F)(F)C(F)OC(F)(F)C(F)(F)C(F)(F)F]

Example 3a

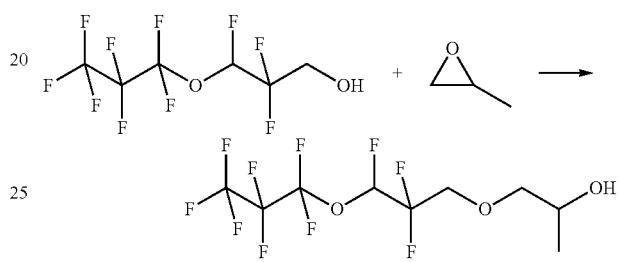

2.0 g of propylene oxide and 13.4 g of 2,2,3-trifluoro-3-heptafluoropropyl-oxypropan-1-ol are initially introduced in a pressure container, and 0.19 g of potassium tert-butoxide in 0.6 g THF is added dropwise. The reaction mixture is subsequently heated at 100° C. for 24 hr.

After cooling to room temperature, 10 ml of water and 10 ml of MTBE are added to the reaction mixture, and the phases are separated. The aqueous phase is extracted with 2×30 ml of MTBE, and the combined organic phase is washed with 40 ml of water and 40 ml of saturated NaCl solution. The extract is dried over sodium sulfate, and the solvent is distilled.

Yield: 14.0 g

1H-NMR: 6.7 ppm (dt, 2H, —CFH); 4.0 (m, 1H, —CH) 3.4-3.6 ppm (m, 4H, CF2-CH2-O—CH2); 2.4 ppm (s, 1H, —COH); 2.0 ppm (d, 3H, —CH3);

Example 3b

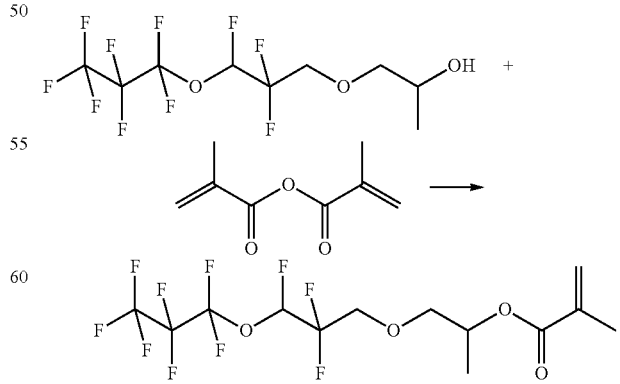

100 ml of toluene, 1.9 g of p-toluenesulfonic acid, 9.3 of methacrylic anhydride and 16.0 g of fluoroalcohol are initially introduced in a two-necked flask. The reaction mixture is subsequently stirred under reflux on a water separator for 6 h.

75 ml of water are added to the mixture, the phases are separated, and the organic phase is in each case washed with 2×20 ml of MTBE. The combined organic phase is dried over sodium sulfate, and the solvent is distilled. The substance is purified by column chromatography.

(silica gel: EA:hexane 1:5)

Yield: 15.0 g

1H-NMR: 6.8 ppm (dt, 2H, —CFH); 6.5 ppm (d, 2H, =CH2); 5.0 ppm (m, 6H, —CH); 3.4-3.6 ppm (m, 4H, CF2-CH2-O—CH2); 2.0 ppm (s, 3H, =C—CH3); 1.4 ppm (d, 3H, —CH3)

Example 4: Synthesis of the Compound of the Formula (VIa)

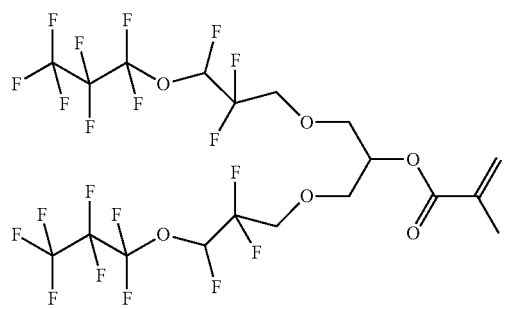

(VIa)

Example 4a

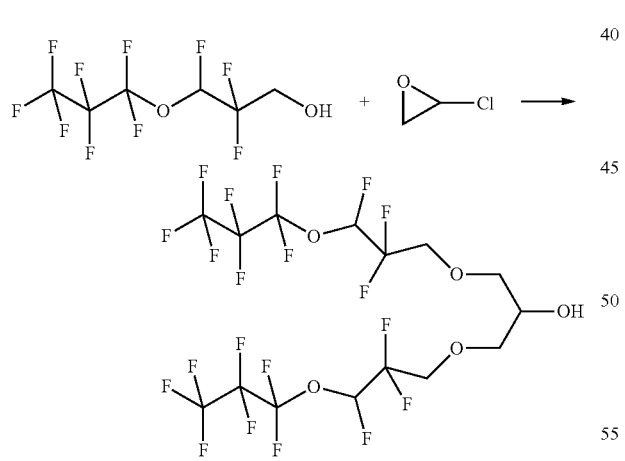

2.13 g of epichlorohydrin and 17.14 g of 2,2,3-trifluoro-3-heptafluoropropyl-oxypropan-1-ol are initially introduced in a two-necked flask. 3.87 g of potassium tert-butoxide in 16 g of THF are added dropwise with cooling.

The reaction mixture is subsequently heated to the boiling temperature and stirred for 24 h.

10 ml of water and 10 ml of MTBE are added to the reaction mixture, and the phases are separated. The aqueous phase is extracted with 2×30 ml of MTBE, and the combined organic phase is washed with 40 ml of water and 40 ml of saturated NaCl solution. The extract is dried over sodium sulfate, and the solvent is distilled.

Product weight: 14.0 g

1H-NMR: 6.7 ppm (m, 2H, —CFH); 4.0 ppm (m, 1H, —CH); 3.6 ppm (m, 4H, CF2-CH2-O—); 3.5 ppm (m, 4H, CH2);

Example 4b

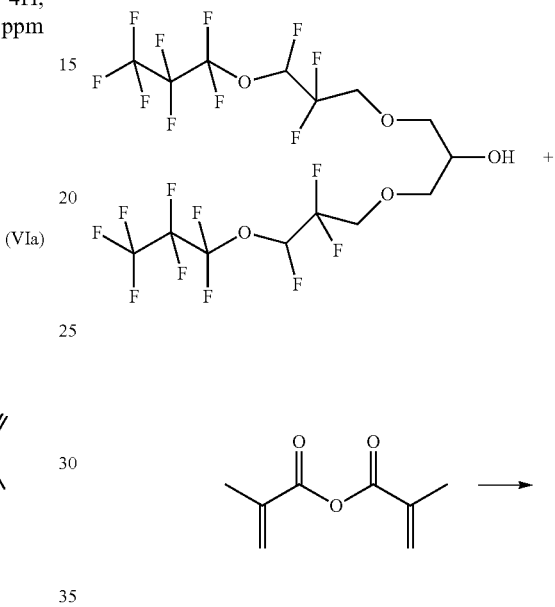

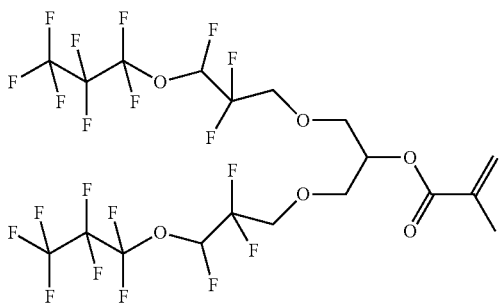

50 ml of toluene, 0.5 g of p-toluenesulfonic acid, 1.8 g of methacrylic anhydride and 15.0 g of fluoroalcohol are initially introduced in a two-necked flask. The mixture is subsequently stirred under reflux on a water separator for 6 h.

35 ml of water are added to the mixture, the phases are separated, and the organic phase is washed in each case with 2×20 ml of MTBE. The combined organic phase is washed with sodium sulfate, and the solvent is distilled. The substance is purified by column chromatography.

(silica gel: EA:hexane 1:5)

Yield 14.2 g

1H-NMR: 6.7 ppm (m, 2H, —CFH); 6.5 ppm (d, 2H, =CH2); 5.0 ppm (m, 1H, —CH); 3.6-3.5 ppm (m, 8H, CF2-CH2-O— and —CH2-C); 2.0 ppm (d, 3H, =C—CH3)

Example 5: Synthesis of the Compound of the Formula (VIIa)

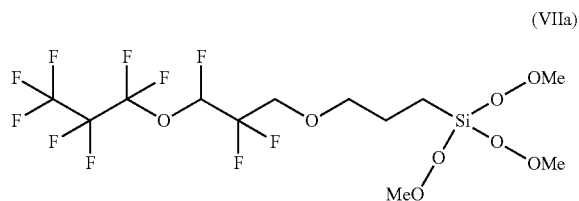 [SMILES: COO[Si](CCCOCC(F)(F)C(F)OC(F)(F)C(F)(F)C(F)(F)F)(OOC)OOC]
(VIIa)

Example 5a

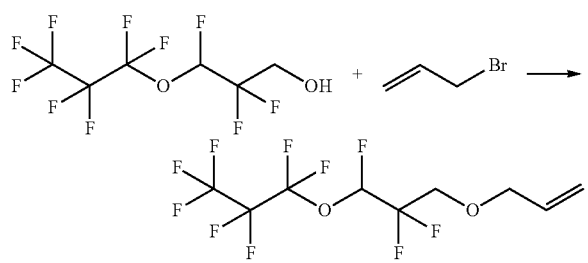

12.3 g of 2,2,3-trifluoro-3-heptafluoropropyloxypropan-1-ol are initially introduced with 2.41 g of sodium methoxide in 11 ml of methanol and heated at the boil for 1 h. 5.0 g of allyl bromide is subsequently added dropwise at RT, and the mixture is warmed under reflux for 24 h.

10 ml of water and 20 ml of MTBE are added to the batch, and the phases are separated. The aqueous phase is extracted with 2×20 ml of MTBE, and the combined org. phases are washed with 25 ml of water.

The solvent is removed in vacuo.

Yield: 8.88 g 60%

1H-NMR: 6.8 ppm (dt, 1H, —CFH); 5.9 ppm (m, 1H, C=CH); 5.3 ppm (m, 2H, C=CH2); 4.1 ppm (m, 2H, —OCH2); 3.8 ppm (m, 2H, —CH2-O)

Example 5b

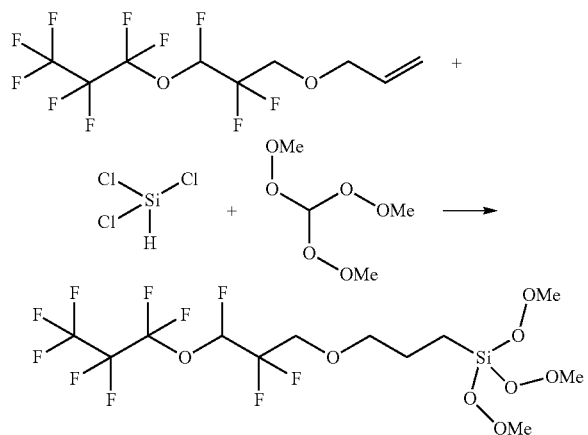

0.15 g of hexachloroplatinic(IV) acid hexahydrate (~40% of Pt) for synthesis and 5 g of 3-(2,2,3-trifluoro-3-heptafluoropropyloxypropoxy)propene in 9.5 ml of dry THF are initially introduced in a 100 ml 4-necked flask with ice cooling and under protective gas. The 2.0 ml of trichlorosilane are slowly added dropwise via a syringe (IT<5° C.). The batch is heated to 56° C. and stirred at this temperature for 4 h. The batch is subsequently cooled to RT under protective gas. 5 ml of trimethyl orthoformate are added to the batch, and 2 ml of MeOH are additionally added. The mixture is heated to 50° C. and stirred at this temperature for 2 h. After cooling, the solvent is distilled and the residue is separated off via a microfilter.

Yield: m=6.60 g 95%

1H-NMR: 6.8 ppm (dt, 1H, —CFH); 3.8 ppm (m, 2H, —OCH2); 3.5 ppm (s, 9H, —OCH3); 3.4 ppm (m, 2H, —CH2O); 1.4 ppm (m, 2H, —CH2); 0.6 ppm (m, 2H, —SiCH2);

Example 6: Synthesis of the Compound of the Formula (VIIIa)

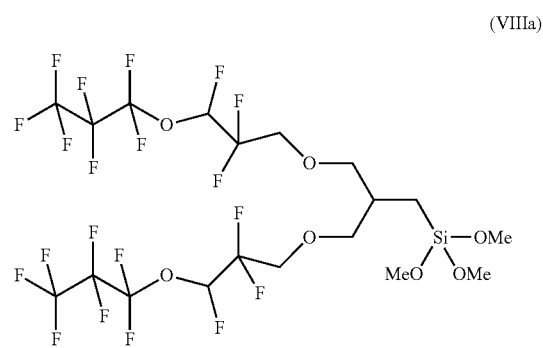 [SMILES: CO[Si](CC(COCC(F)(F)C(F)OC(F)(F)C(F)(F)C(F)(F)F)COCC(F)(F)C(F)OC(F)(F)C(F)(F)C(F)(F)F)(OC)OC]
(VIIIa)

Example 6a

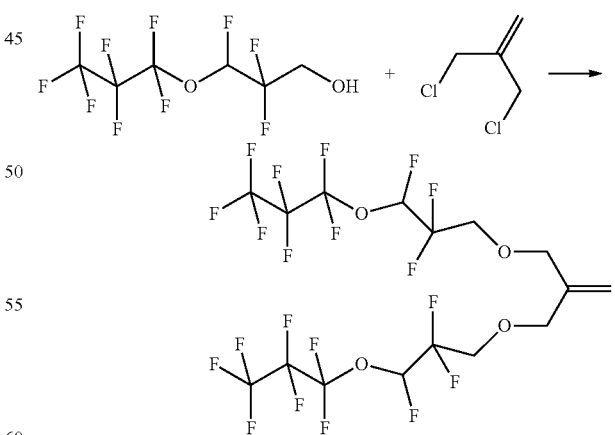

15.3 g of 2,2,3-trifluoro-3-heptafluoropropyloxypropan-1-ol and 3.0 g 3-chloro-2-chloromethylpropene are heated at the boil with 4.0 g of potassium hydroxide and 20 ml of toluene for 24 h.

After cooling, the precipitate is filtered off with suction, 20 ml of water and 20 ml of MTBE are added to the filtrate, and the phases are separated. The aqueous phase is extracted with 2×20 ml of MTBE, and the combined organic phases are again washed with 20 ml of water and dried over sodium sulfate. The solvent is distilled in vacuo. Crude yield: m=7.1 g The product is purified in a high vacuum.

B.p.: 42-45° C. at 4.8 10-2 mbar m: 6.5 g

1H-NMR: 6.8 ppm (dt, 2H, —CFH); 5.15 ppm (d, 2H, =CH2); 4.05 ppm (s, 4H, —OCH2-C=); 3.75 ppm (m, 4H, —CF2-CH2O)

Example 6b 0.15 g of hexachloroplatinic(IV) acid hexahydrate (~40% of Pt) for synthesis and 6.5 g of bis 3-(2,2,3-trifluoro-3-heptafluoropropyloxypropoxy)propene in 9.5 ml of dry THF are initially introduced in a 100 ml 4-necked flask with ice cooling and under protective gas. The 1.2 ml of trichlorosilane are slowly added dropwise (IT<5° C.). The batch is heated to 56° C. and stirred at this temperature for 4 h. The batch is subsequently cooled to RT under protective gas. 3.5 ml of trimethyl orthoformate are added to the batch, and 1 ml of MeOH is additionally added. The mixture is heated to 50° C. and stirred at this temperature for 2 h. After cooling, the solvent is distilled and the residue is separated off via a microfilter. The yellowish oil is dried in a high vacuum Yield: m=5.2 g 75%

1H-NMR: 6.8 ppm (dt, 2H, —CFH); 3.8-4.1 ppm (m, 9H, —CH2-); 3.5 ppm (s, 9H, —OCH3); 0.6 ppm (m, 2H, —SiCH2)

The invention claimed is:
1. A compound of the formula (I)

$$(Rf\text{-}CHF\text{—}CF_2\text{—}CHR)_m\text{-}L\text{-}(X)_n \quad (I)$$

where
a)
   Rf is a group selected from $CF_3$—$(CF_2)_{0-3}$—O—$(CF_2)_{1-3}$—, $CF_3$—$(CF_2)_{0-3}$—O—$(CF_2)_{1-3}$—O—, $CF_3$—$(CF_2)_{0-3}$—O—$(CF_2)_{1-3}$—O—$CF_2$—, $CF_3$—$(CF_2)_{0-3}$—O—$(CF_2$—O$)_{1-8}$ and $CF_3$—$(CF_2)_{0-3}$—O—$(CF_2$—O$)_{1-8}$—$CF_2$—
   R=H or an alkyl group,
   L=a single bond or a saturated, branched or unbranched alkylene group, optionally containing heteroatoms and/or functional groups,
   X=an ethylenically unsaturated group, an alkoxysilane group, a silanol group or a halosilane group,
   m is ≥1
   and n is ≥1
   or
b)
   Rf is $CF_3$—$(CF_2)_{0-3}$—,
   R=an alkyl group,
   L=a single bond or a saturated, branched or unbranched alkylene group, optionally containing heteroatoms and/or functional groups,
   X=an alkoxysilane group, a silanol group or a halosilane group,
   m is ≥1
   and n is ≥1,
   or
c)
   Rf is where $CF_3$—$(CF_2)_{0-3}$—O— the compounds conform to the formulae (III) to (VIII) where R"=$C_1$-$C_4$-alkyl and R'"=H or an alkyl group, -continued

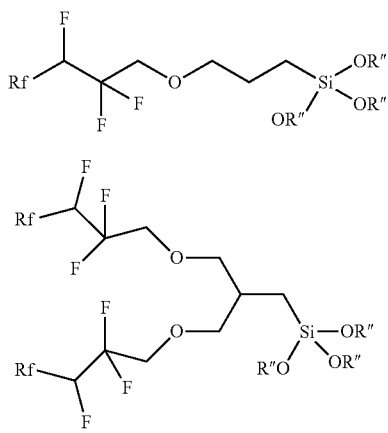

where R″=C1-C4-alkyl and R‴=H or an alkyl group.

2. A compound according to claim 1, wherein Rf is $CF_3-(CF_2)_{1-2}-O-$, $CF_3-O-(CF_2)_{1-2}-$, $CF_3-O-(CF_2)_{1-3}-O$, $CF_3-(CF_2)_{1-2}-O-CF_2-$, $CF_3-O-(CF_2)_{1-2}-O-CF_2-$, $CF_3-O-(CF_2-O)_{1-8}-$ and $CF_3-O-(CF_2-O)_{1-8}-CF_2-$.

3. A compound according to claim 1, wherein R in a) is equal to H or C1-C3 alkyl.

4. A compound according to claim 1, wherein R in a) is equal to H or a methyl group.

5. A compound according to claim 1, wherein L is a saturated, branched or unbranched alkylene group, optionally containing heteroatoms and/or functional groups.

6. A compound according to claim 1, wherein X is an ethylenically unsaturated group, an alkoxysilane group, or a halosilane group.

7. A compound according to claim 1, wherein X is an acrylate or methacrylate group.

8. A compound according to claim 1, wherein X is equal to —SiR′$_3$, where the groups R′ are, independently of one another, equal to alkyl, OH, halogen, alkoxy or aryloxy, where at least one group R′ is not an alkyl group.

9. A compound according to claim 8, wherein R′ an alkoxy group OR″, where R″ equal to C1-C4-alkyl.

10. A compound according to claim 9, wherein R″ is equal to C1- or C2-alkyl.

11. A compound according to claim 1, wherein m and n, independently of one another, are equal to 1-3.

12. A compound according to claim 1, of formulae

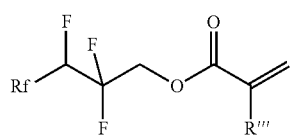

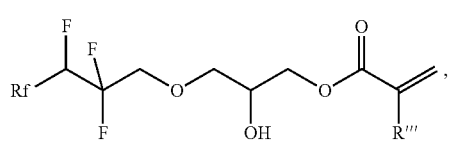

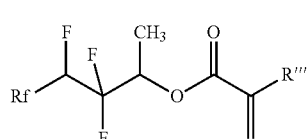

-continued

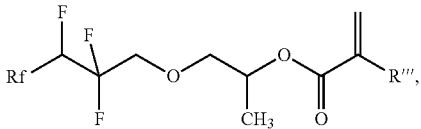

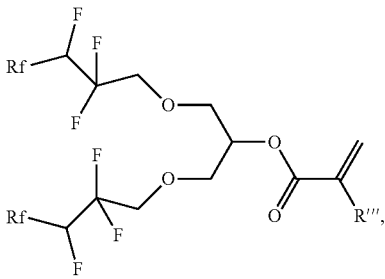

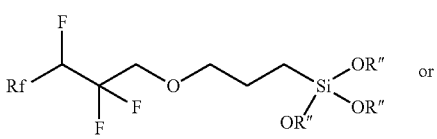

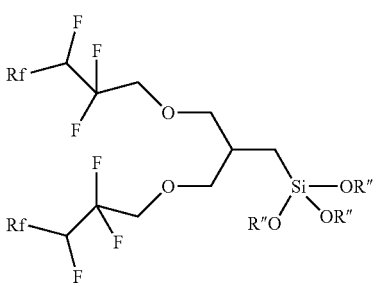

where Rf=a group selected from $CF_3-(CF_2)_{0-3}-O-(CF_2)_{1-3}-$, $CF_3-(CF_2)_{0-3}-O-(CF_2)_{1-3}-O-$, $CF_3-(CF_2)_{0-3}-O-(CF_2)_{1-3}-O-CF_2-$, $CF_3-(CF_2)_{0-3}-O-(CF_2-O)_{1-8}-$ and $CF_3-(CF_2)_{0-3}-O-(CF_2-O)_{1-8}-CF_2-$, R″=C1-C4-alkyl and R‴=H or an alkyl group.

13. A compound according to claim 12, wherein Rf is equal to $CF_3-(CF_2)_{1-2}-O-$, $CF_3-O-(CF_2)_{1-2}-$ or $CF_3-O-(CF_2)_{1-3}-O-$.

14. A compound according to claim 1, that is

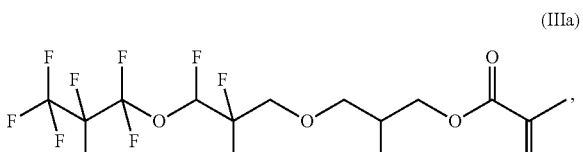

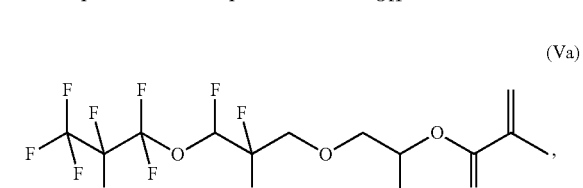

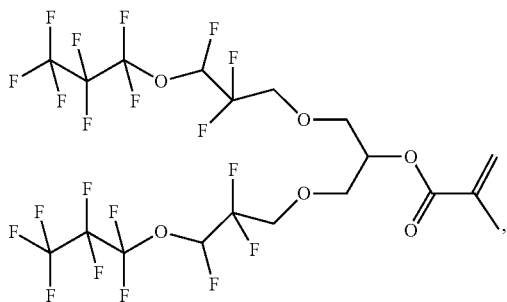

(VIa)

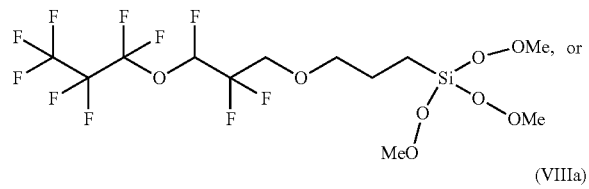

(VIIa)

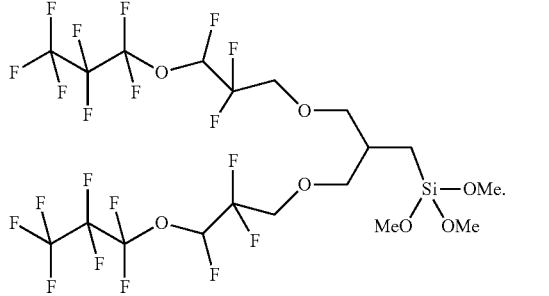

(VIIIa)

15. A composition comprising at least one compounds according to claim 1 and a support which is suitable for the respective application and optionally further additives.

16. A coated article whose coating has been produced using at least one compound according to claim 1.

17. A method for the production of functional coatings and surface modifications, which comprises including a compound according to claim 1 in a functional coating or surface modification.

18. A process for the degradation of fluorine-containing compounds of claim 1 comprising the following steps:
   a) biological and/or abiotic degradation of the carbon skeleton of the fluorine-containing compounds with formation of fluorine-containing compounds,
   b) conversion of the fluorine-containing compounds formed in step a) into a gas phase,
   c) degradation of the fluorine-containing compounds formed in step a) into low-molecular-weight compounds by UV irradiation in the gas phase,
   d) conversion of the low-molecular-weight compounds formed in step c) from the gas phase into a liquid and/or solid phase,
   e) mineralisation of the low-molecular-weight compounds formed in step c) in the liquid and/or solid phase.

* * * * *